United States Patent [19]
Dürr et al.

[11] Patent Number: 4,983,324
[45] Date of Patent: Jan. 8, 1991

[54] PYRROLO(1,2-B)AZINES

[75] Inventors: Heinz Dürr, Saarbrücken-Schafbrücke; Volker Bach, Kirkel, both of Fed. Rep. of Germany

[73] Assignee: Merck Patent Gesellschaft mit Beschrankter Haftung, Darmstadt, Fed. Rep. of Germany

[21] Appl. No.: 283,997

[22] Filed: Nov. 25, 1988

[30] Foreign Application Priority Data

Apr. 10, 1987 [DE] Fed. Rep. of Germany ...... 3710889
Mar. 21, 1988 [WO] PCT Int'l Appl. .. PCT/EP88/00229

[51] Int. Cl.$^5$ .......................... E21V 9/04; G02B 6/10
[52] U.S. Cl. ..................................... 252/587; 252/582; 350/96.12; 350/96.3
[58] Field of Search ...................... 252/582, 589, 587; 350/96.12, 96.3

[56] References Cited

FOREIGN PATENT DOCUMENTS

| | | |
|---|---|---|
| 2906193 | 8/1980 | Fed. Rep. of Germany . |
| 3220257 | 12/1983 | Fed. Rep. of Germany . |
| 3320077 | 12/1984 | Fed. Rep. of Germany . |
| 3320077 | 12/1984 | Fed. Rep. of Germany . |
| 3521432 | 12/1986 | Fed. Rep. of Germany . |
| 8807702 | 10/1988 | World Int. Prop. O. .......... 252/587 |

OTHER PUBLICATIONS

Patterson, A. M., Capell, L. T., and Walker, D., The Ring Index: A List of Ring Systems Used in Organic Chemistry, 2nd ed., 1960, p. 167.
DeBlauwe, V. et al., J. Polym. Sci/A-Polym. Chem. 27(2), 671, 1989.
Durr, H. et al, Angew. Chem. 96(3) 227–9, 1984.
Durr, H. et al, Angew Chem 91(12) 1010–11, 1979.
Meredith, G.; Williams, D. in Nonlinear Opt. Prop. Org. Polym. Materials, D. J. Williams, ed. A.C.S., Washington, DC 1983, ch. 6.

*Primary Examiner*—Robert L. Stoll
*Assistant Examiner*—Richard Treanor
*Attorney, Agent, or Firm*—Millen, White & Zelano

[57] ABSTRACT

Non-linear optical materials contain the structural elements of the general formula I and/or I'

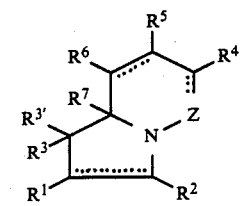

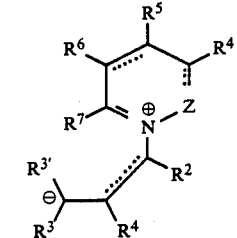

in which $R^1$, $R^2$, $R^3$, $R^{3'}$, $R^4$, $R^5$, $R^6$, $R^7$ and Z have the meaning indicated in patent claim 1.

13 Claims, No Drawings

PYRROLO(1,2-B)AZINES

BACKGROUND OF THE INVENTION

The invention relates to new polymer materials having non-linear optical properties and to processes for their preparation.

Non-linear optics deals with the interaction of electromagnetic fields in various media and the consequent formation of new fields with altered properties. Materials having non-linear optical properties possess a field strength-dependent dielectric susceptibility of the 2nd order which has a series of dispersive processes as a consequence: the frequency doubling (second harmonic generation=SHG) permits the production of light of half the wavelength compared with the irradiating light; the electrooptical effect (Pockels effect) makes possible a change in the refractive index with applied electrical field; methods of sum and difference frequency mixing and frequency splitting allow the continuous tuning of laser light.

A large number of technological applications result from the previously mentioned effects. Electrooptical switches, frequency and intensity control in laser technology, holography and the areas of information processing and integrated optics represent areas of use for materials having non-linear optical properties of the 2nd order.

Materials having electrical susceptibility functions of the 3rd order are suitable for the preparation of purely optical switches and thus as waveguides for construction of purely optical computers.

In order to be suitable for application in the area of non-linear optics of the 2nd order, materials of this type have to fulfil a number of requirements.

In addition to a non-centrosymmetrical molecular arrangement in the crystal, technological utility calls for as high as possible a value for the dielectric susceptibility $X^{(2)}$.

A number of inorganic substances such as, for example, potassium dihydrogen phosphate or lithium niobate show non-linear optical properties. However, all these compounds are affected by all sorts of disadvantages. In addition to insufficient values for the dielectric susceptibility of the second order, inorganic compounds frequently lack sufficient photostability on treatment with high light intensities, or they can only be prepared and processed with difficulty.

Organic compounds of the nitroaniline type are known from Garito et al., Laser Focus 18 (1982) and EP-0,091,838. However, their relatively good values for photochemical stability and dielectric susceptibility of the second order go along with poor crystallizability and deficient mechanical stability. In particular, the preparation of thin layers, such as are required for integrated optics, is unsuccessful with these materials.

Polymers are characterized by high mechanical resistance capabilities and good chemical stability. Molecules having non-linear optical properties which are attached to the polymer framework or dissolved in the polymers should therefore have advantageous values for dielectric susceptibility in the non-centrosymmetrical environment.

Polymers having non-linearities of the second order can be prepared by applying an external field to a film heated above the glass temperature and doped with randomly orientated molecules. This leads to a polarization of the included molecules which confers an anisotropy to the polymer medium after solidification thereof. Polymers having non-linear optical properties prepared in this manner, in which p,p'-dimethylaminonitrostilbene is used as the host molecule, were described by Meredith et al., Macromolecules 15 (1982) 1385.

Shibaev et al., Polymer Communications 24 (1983) 364, report the field-induced alignment of liquid crystal polymers with mesogenic side groups.

U.S. Pat. No. 4,412,059 discloses a polymer material having cholesteric mesophases which are accessible by means of electrical or magnetic fields of a controlled alignment. Finally, fully aromatic, thermotropic, liquid crystal polymers are known from EP-0,172,012, the non-linear optical properties of which can likewise be produced by external fields.

A further method for the production of polymer materials having non-linear optical properties consists in the polymerization of monomers which are already ordered and have a non-centrosymmetric orientation, the state of order of the system being essentially maintained during the polymerization. Suitable monomers for this technique are to be taken, for example, from EP-0,021,695.

The materials described previously still show unsatisfactory non-linear optical properties which are expressed in particular in deficient values for the dielectric susceptibility and the photochemical stability.

SUMMARY OF THE INVENTION

A need thus exists for materials having non-linear optical properties which do not exhibit the disadvantages described or only to a small degree.

This object is achieved by the non-linear optical materials according to the invention.

The invention therefore relates to non-linear optical materials, which comprise at least one component having the structural element of a pyrrolo[1 2-b]azine of the formula I and/or its valence isomers of the formula I'

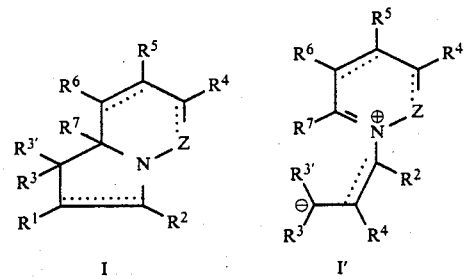

in which one of the double bonds represented as dashed can be a single bond between the positions 2-3, 5-6 and 7-8, and $R^1$ is $C_1$-$C_{10}$ alkoxycarbonyl, $C_1$-$C_{10}$ alkanoyl, $C_7$-$C_{11}$ aroyl, —CN, —CF$_3$, —N($C_{1-4}$ alkyl)$_2$ or H, if $R^2$ is not also H at the same time, $R^2$ is H or a radical $R^1$, $R^3$ and $R^{3'}$ are a radical completing a dibenzocyclopentadiene, dichlorodibenzocyclopentadiene, monobenzodiphenylcyclopentadiene, tetraphenylcyclopentadiene or dibenzocyclohexa-2,5-diene-4-one ring, or its 4-thione, 4-($C_{1-4}$ alkyl)imino or 4-ethylidene derivative, or of a dibenzo-γ-pyran ring, phenyl, $C_1$-$C_{10}$ alkoxycarbonyl, $C_1$-$C_{10}$ alkanoyl, indan-1,3-dione-2,2-diyl, 2,2-dimethyl-1,3-dioxane-4,6-dione-5,5-diyl 4-nitrophenyl, 4- cyanophenyl or $C_1$-$C_{10}$ alkoxypropenoyl, or one of the radicals is also H, $R^4$ is H, $C_1$-$C_{10}$ alkyl or, together with $R^5$, a radical completing a fused cyclopentane or cyclohexane ring, $R^5$ is H, $C_1$-$C_{10}$ alkyl, $C_{1-10}$ alkoxy $C_{1-10}$ alkoxycarbonyl, —CN, —CH$_2$Ph, —COPh, —CONH$_2$, —CON—($C_{1-4}$ alkyl)$_2$, —CONH($C_{1-4}$ alkyl) or, together with $R^4$, is a radical completing a fused cyclopentane or cyclohexane ring or, together with $R^6$, a radical completing a fused benzene ring, $R^6$ is H, $C_{1-10}$ alkyl or, together with $R^5$, a radical completing a fused benzene ring or, together with $R^7$, a radical completing a fused cyclopentane or cyclohexane ring, $R^7$ is H, $C_{1-10}$ alkyl or, together with $R^6$, a radical completing a fused cyclopentane or cyclohexane ring and Z is —N=, —CR$^4$= or —CHR$^4$—.

Pyrrolo[1.2-b]azines have been disclosed, for example, in DE-A1-2,906,193 and DE-A1-3,220,257. In these publications, the use of the compounds of the formula I as radiation-sensitive materials for measurement, recording and storage purposes is described.

The compounds of the formula I undergo on irradiation, in particular with short wavelength visible light or UV light, a tranformation in their valence isomers of the formula I'. From compounds containing the structural element of the formula I, merocyanine-like forms of the formula I' formed undergo a stabilization of both the negative and the positive charge by monocyclic aromatic or heteroaromatic ions and/or by suitable electron donor or acceptor substituents.

Surprisingly, it has now been found that compounds of this type are also suitable in a preferred manner as components of materials having non-linear optical properties. Layers of monomeric compounds of the formula I and/or I', polymer compositions having such compounds included and polymers having chemically bonded structural units of the formula I and/or I' are equally suitable for this purpose.

Pyrrolo[1.2-b]azines of the formula I and/or I', in which all dashed bonds are double bonds, are particularly suitable. $R^1$ and $R^2$ are preferably $C_1$-$C_{10}$ alkoxycarbonyl —CN or —N($C_1$-$C_{14}$ alkyl)$_2$, in particular $C_1$-$C_{10}$ alkoxycarbonyl or —CN. $R^3$ and/or $R^{3'}$ are preferably a substituent stabilizing a negative charge such as, for example, $C_1$-$C_{10}$ alkoxycarbonyl, phenyl, substituted phenyl, in particular 4-nitrophenyl or 4-cyanophenyl, in addition also to a radical completing a dibenzocyclopentadiene, dichlorodibenzocyclopentadiene, tetraphenylcyclopentadiene or dibenzocyclohexa-2,5-dien-4-one ring, in particular a dibenzocyclopentadiene ring. The radicals $R^3$ and $R^{3'}$ can be identical or different, preferably they are identical. $R^4$ is preferably H, $C_{1-10}$ alkyl, in particular $C_1$-$C_4$, and, together with $R^5$, is a radical completing a cyclopentane or cyclohexane ring.

$R^5$ is preferably H, $C_1$-$C_{10}$ alkyl or $C_1$-$C_{10}$ alkoxycarbonyl, —CN, —CH$_2$Ph, —COPh, —CONH$_2$, or, together with $R^4$, is a radical completing a cyclopentane or cyclohexane ring or, together with $R^6$, is a radical completing a benzene ring.

Preferably, $R^6$ is H, $C_1$-$C_5$ alkyl, or, together with $R^5$, a radical completing a benzene ring or, together with $R^7$, a radical completing a cyclohexane ring. Preferably, $R^6$ is H.

$R^7$ is preferably H, $C_1$-$C_5$ alkyl, or, together with $R^6$, is a radical completing a cyclohexane ring. In particular, Z is —N=, and in addition also —CR$^4$=.

If desired, the alkyl radicals mentioned can also be substituted. The aromatic hydrocarbon groups present as substituents or in fused form can likewise carry further substituents. In particular, the following substituents are quite generally suitable, if the question here or in the following is of substitution: $C_{1-4}$ alkyl, $C_{1-4}$ alkoxy, halogen (fluorine, chlorine, bromine and iodine), —CF$_3$, —NO$_2$, —N($C_{1-4}$-alkyl)$_2$ and $C_{6-10}$ aryl. However, other substituents are also utilizable.

Accordingly, in particular those compounds of the general formula I and/or I' in which are least one of the radicals $R^1$, $R^2$, $R^3$, $R^4$, $R^5$, $R^6$, $R^7$ or Z has one of the previously mentioned meanings are preferably used according to the invention as non-linear optical media.

The compounds of the formula I can be prepared by known processes, such as are described, for example, in DE-A1-2,906,193 or in DE-A1-3,220,257. A preferred process for their preparation consists in the reaction of cyclopropenes II or pyrazoles III

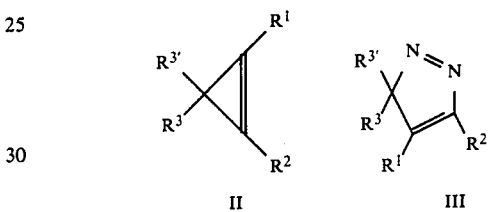

having the previously mentioned meanings for $R^1$, $R^2$, $R^3$ and $R^{3'}$, with an azine of the formula IV

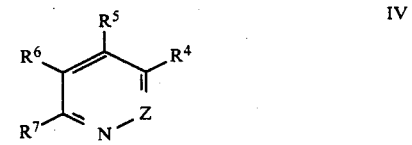

in which $R^4$, $R^5$, $R^6$, $R^7$ and Z have the previously mentioned meanings, in the manner described in DE-A1-3,521,432 under the reaction conditions indicated therein. The preparation of the necessary starting materials is likewise to be taken from DE-A1-3,521,432.

Components containing the structural element of the merocyanine-like form according to formula I' are particularly suitable for use in non-linear optical materials. If, in their preparation from the compounds of the formula I by irradiation with light of suitable wavelength, an electrical field is applied at the same time, then the polar structures of the formula I' obtained orientate themselves according to the field direction and lead to a molecular association without a symmetry inversion center and thus non-linear optical properties.

The pyrrolo[1.2-b]azines of the formula I and/or I' are outstandingly suitable as non-linear optical media. Thus, for example, by applying compounds of this type to a substrate in dissolved or liquid form by, for example, brushing, printing, dipping or centrifuging and, if desired, subsequent irradiation under the action of an electrical field, non-linear optical arrangements are obtained which, for reasons of their advantageous properties, open up a wide field of application. In particular, they are suitable for frequency doubling of laser light and for preparation of switch elements, waveguides and phase modulators from the area of integrated optics.

The compounds of the formula I and/or I' can furthermore also exhibit their non-linear optical properties in powder form, as inclusions in other molecular associations, such as, for example, clathrates, solid solutions, or as single crystals or solutions.

The present invention further relates to the inclusion of compounds of the formula I and/or I' in polymers. To this end, compounds of the general formula I can be incorporated, for example, into solutions of suitable polymer materials, such as are described, for example in EP-A2-0,194,639 as utilizable for the preparation of waveguides. Doped polymer solutions thus obtained and also correspondingly doped polymer melts can be applied to substrates by the same techniques described previously and, if desired, converted into the valence isomers of the formula I' by irradiation under the action of an electrical field.

The present invention further relates to a non-linear optical polymer material which contains structural units of the general formula I and/or I' optionally bonded chemically to the polymer chain via connecting groups (spacers).

Materials of this type contain, for example, recurring structural units of the general formula I and/or I', in which at least one of the radicals $R^1$, $R^2$, $R^3$, $R^{3'}$, $R^4$, $R^5$, $R^6$, $R^7$ or Z corresponds to the formula V $$-Y-X-A- \qquad V$$

in which
Y is $-(CH_2)_n-$ or $-CH(CH_3)-$,
X is a chemical bond, $-O-$, $-S-$, $-NR-$, $-SO-$, $-SO_2-$, $-CO-$, $-O-CO-$, $-CO-O-$, $-S-CO-$, $-CO-S-$, $-NR'-CO-$ or $-CO-NR'-$,
A is $C_1-C_{20}$ alkylene, in which one or more non-adjacent $CH_2$ groups can also be replaced by $-O-$, $-S-$ and/or $-NR^1-$,
R' is H or $C_{1-4}$ alkyl and
n is 0, 1, 2 or 3.

The bond of the pyrrolo[1.2-b]azine unit to the polymer chain occurring via the radical A can occur via a chemical bond or via $-CO-O-$, $O-CO-$, $-NR'-CO-$, $-CO-NR'-$, $-NH-CO-O-$, $-NH-CO-NR'-$, $-O-CO-NH-$ or $-NR'-$.

Suitable spacers are, above all, alkylene groups having 2 to 20 C atoms which linear or branched and in which can be one or more $CH_2$ groups can be replaced by $-O-$, $-S-$ and/or $-NR'-$.

Suitable spacers are, for example:
ethylene, propylene, butylene, pentylene, hexylene, octylene, decylene, undecylene, dodecylene, octadecylene, ethyleneoxyethylene, ethylenethioethylene, ethylene-N-methyliminoethylene or 1-methylalkylene.

The spacers can be bonded to the pyrrolo[1.2-b]azine moiety and to the polymer chain via a chemical bond or via $-CO-O-$, $-O-CO-$, $-NR'-CO-$, $-CO-NR'$, $-NH-CO-O-$, $-NH-CO-NR'-$, $-O-CO-NH-$ or $-NR'-CO-NH-$.

Y is preferably $-CH(CH_3)-$, methylene, ethylene or a direct bond. X is preferably $-O-$, $-CO-O-$, $-O-CO-$, $-NH-CO-$, $-CO-NH-$, $-O-CO-NH$ or $-NH-CO-O-$. $C_4-C_{12}$ alkylene is preferred for A. R' is preferably H or methyl.

The polymers which contain chemically bonded pyrrolo[1.2-b]azine units can be prepared by processes which are known per se and which are customary in polymer chemistry.

Thus, pyrrolo[1.2-b]azine units having a terminal hydroxyl, mercapto or amino group on a radical $R^1$, $R^2$, $R^3$, $R^{3'}$, $R^4$, $R^5$, $R^6$, $R^7$ or Z can be introduced, for example, into polymeric compounds of the formula VI

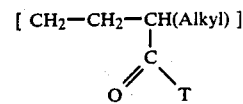

in which T is an exchangeable radical such as hydroxyl, chlorine or lower alkoxy, by esterification, transesterification or acylation.

The methods are known per se and can, for example, be taken from C. M. Paleos et al., J. Polym. Sci. Polymer. Chem. Ed. 19 (1981) 1427.

The exchange of T can also be carried out using a reactive group of a spacer bonded to the pyrrolo[1.2-b]azine unit.

In such radicals, in which one of the substituents $R^1$, $R^2$, $R^3$, $R^{3'}$, $R^4$, $R^5$, $R^6$, $R^7$ or Z carries a terminal carboxyl group or functional groups thereof, the polymers must contain amino, mercapto or hydroxyl groups.

Such polymers can be obtained, for example, by copolymerization of (meth)acrylic acid hemiesters of 1,ω-diols with further comonomers.

A further possibility of binding pyrrolo[1.2-b]azine groups to the polymer chain consists in the reaction of these groups carrying an isocyanate radical with polymers which have substituents reacting with isocyanates, for example the hydroxyl group-carrying copolymers mentioned previously.

The isocyanate radical can be introduced into a compound of the formula I and/or I', for example, by reacting a substituent reacting with isocyanate such as, for example, a pyrrolo[1.2-b]azine carrying $-OH$, $-SH$ or $-NH_2$ on one of the radicals $R^1$, $R^2$, $R^3$, $R^{3'}$, $R^4$, $R^5$, $R^6$, $R^7$ or Z, with a diisocyanate in the molar ratio 1:1.

The reaction of the compounds of the formula I and/or I' carrying an isocyanate radical with the polymer carrying the reactive substituent is carried out by a process known per se.

Conversely, it is also possible to introduce isocyanate radicals into polymers and to react the isocyanate radicals with compounds of the formula I and/or I' which carry a terminal substituent reacting with isocyanate on one of the radicals $R^1$, $R^2$, $R^3$, $R^{3'}$, $R^4$, $R^5$, $R^6$, $R^7$ or Z.

Polymers which carry pyrrolo[1.2-b]azines bonded in the side chain or on to the side chain can also be prepared by synthesizing, for example, pyridazyl compounds in the 4-position using a polymerizable radical, preferably an acrylate, and then initially homo- or copolymerizing. The pyrroloazine framework is subsequently synthesized by reaction with a cyclopropene II.

The polymers can additionally be prepared by copolymerization of ethylenically unsaturated compounds of the formula (VII)

if desired with further olefinically unsaturated compounds which are copolymerizable with (VII).

In formula (VII), W is a pyrrolo[1.2-b]azine of the formula I and/or I' optionally bonded via a spacer to the C atom of the carbonyl radical, the bonding taking place via —O—, —S—, or —NR'—.

The degree of polymerization is as a rule between 5 and 500, preferably ≧10 and 100.

Suitable monomers are, above all:

$C_1$- to $C_{20}$-, preferably $C_4$- to $C_8$-, alkyl esters of acrylic acid and/or methacrylic acid, mixtures of these esters and mixtures of the esters mentioned with acrylonitrile, methylacrylonitrile, styrene, 4-methylstyrene, acrylamide and/or methacrylamide.

Suitable monomers in addition to those specifically mentioned in detail are, for example:

methyl acrylate, ethyl acrylate, propyl acrylate, n-butyl acrylate, isobutyl acrylate, hexyl acrylate, n-octyl acrylate, 2-ethylhexyl acrylate, nonyl acrylate, decyl acrylate, dodecyl acrylate, hexadecyl acrylate, octadecyl acrylate and the corresponding methacrylates.

The acrylates and methacrylates of alkanols up to 8 C atoms mentioned are preferred.

The preparation of the polymers is carried out by known processes, preferably by free radical polymerization.

They can additionally be obtained by addition of polarizable, reactive radicals carrying hydrogen to olefinic double bonds.

Thus, compounds of the formula I and/or I' containing polyorganohydrogensiloxanes with a terminal vinyl group can optionally be reacted, for example, in solvents in the presence of catalysts, in particular hexachloroplatinic acid, which accelerate the addition of hydrogen bonded to Si to aliphatic multiple bonds.

These reactions are carried out in a manner known per se (H. Ringsdorf, A. Schneller; Brit. Polym. Journal 13, 43 (1981); H. Ringsdorf, A. Schneller; Makromol Rapid Comm. Vol. 3, 557 (1982)).

The polymer materials according to the invention open up, for reasons of their advantageous non-linear optical properties, a wide application field. In particular, they are suitable for frequency doubling of laser light and for the preparation of switch elements, waveguides and phase modulators from the area of integrated optics.

EXAMPLES

The following examples serve to illustrate the invention:

A. Preparation of the compounds (a) Preparation of spiro-3H-pyrazoles III 2 g of the diazofluorene derivatives are dissolved in anhydrous ether and equimolar amounts of the corresponding alkyne esters are added dropwise with stirring. The reaction mixture is stirred in a darkened vessel at room temperature and the course of the reaction is checked by means of thin layer chromatography (TLC). After completion of the reaction, the solvent is stripped off under reduced pressure. The residue is recrystallized.

(b) Preparation of spirocyclopropenes II 2 g of the spiro-3H-pyrazoles III are dissolved in 300 ml of anhydrous ether and irradiated in a photolysis apparatus at room temperature until TLC checking and the amount of nitrogen evolved indicates complete reaction. After concentrating the solution under reduced pressure, the crystals are formed in the cold.

(c) Preparation of pyrroloazines I by nucleophilic addition of the heterocycles IV to the spirocyclopropenes II.

1 mmol of the spirocyclopropenes II are reacted in dry ether with 1–2 mol equivalents of the heterocycles IV. A coloration of the reaction solution indicates the formation of the betaines. Further stirring at room temperature with exclusion of light leads with decolorization to the formation of the pyrrolo(1,2-b)-azines I which are obtained pure by recrystallization after working up by chromatography (silica gel/$CH_2Cl_2$).

1'H-Pyrrolo[1.2-b]pyridazines Ia from the compounds II or III

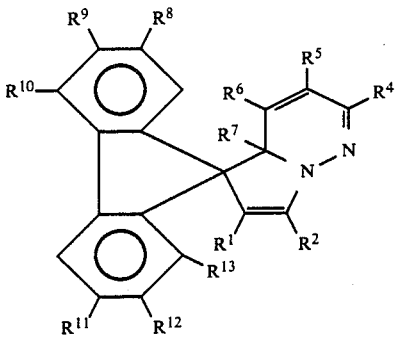

Ia

| No. | $R^1/R^2$ | $R^4$ | $R^5$ | $R^6$ | $R^7$ | $R^8$ | $R^9$ | $R^{10}$ | $R^{11}$ | $R^{12}$ | $R^{13}$ | m.p. [°C.] | Prepared from |
|-----|-----------|-------|-------|-------|-------|-------|-------|----------|----------|----------|----------|------------|---------------|
| 1 | $CO_2C_3H_7$ | H | H | H | H | H | H | H | H | H | H | 120 | II |
| 2 | $CO_2C_4H_9$ | H | H | H | H | H | H | H | H | H | H | 97 | II |
| 3 | $CO_2C_5H_{11}$ | H | H | H | H | H | H | H | H | H | H | 80 | II |
| 4 | $CO_2C_6H_{13}$ | H | H | H | H | H | H | H | H | H | H | 69 | II |
| 5 | $CO_2C_7H_{15}$ | H | H | H | H | H | H | H | H | H | H | 51 | II |
| 6 | $CO_2C_3H_7$ | $CH_3$ | H | H | $CH_3$ | H | H | H | H | H | H | 153 | II |
| 7 | $CO_2C_4H_9$ | $CH_3$ | H | H | $CH_3$ | H | H | H | H | H | H | 117 | II |
| 8 | $CO_2C_5H_{11}$ | $CH_3$ | H | H | $CH_3$ | H | H | H | H | H | H | 98 | II |
| 9 | $CO_2C_6H_{13}$ | $CH_3$ | H | H | $CH_3$ | H | H | H | H | H | H | 82 | II |
| 10 | $CO_2C_7H_{15}$ | $CH_3$ | H | H | $CH_3$ | H | H | H | H | H | H | 74 | II |
| 11 | $CO_2C_5H_{11}$ | $CH_3$ | $CH_3$ | H | $CH_3$ | H | H | H | H | H | H | 108 | II |

-continued

1'H-Pyrrolo[1.2-b]pyridazines Ia from the compounds II or III

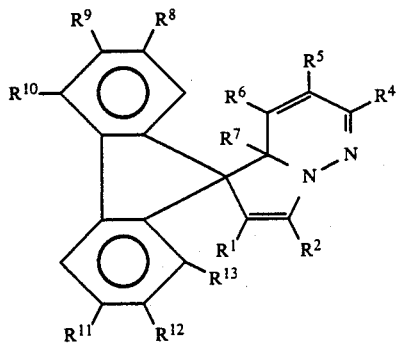

| No. | R¹/R² | R⁴ | R⁵ | R⁶ | R⁷ | R⁸ | R⁹ | R¹⁰ | R¹¹ | R¹² | R¹³ | m.p. [°C.] | Prepared from |
|---|---|---|---|---|---|---|---|---|---|---|---|---|---|
| 12 | CO₂C₅H₁₁ | CH₃ | CH₃ | CH₃ | CH₃ | H | H | H | H | H | H | 146 | II |
| 13 | CO₂C₅H₁₁ | H | Benzo | | H | H | H | H | H | H | H | 68 | II |
| 14 | CO₂C₄H₉ | H | CH₃ | H | H | H | H | H | H | H | H | 89 | II |
| 15 | CO₂C₅H₁₁ | H | CH₃ | H | H | H | H | H | H | H | H | 73 | II |
| 16 | CO₂CH₃ | CH₃ | CO₂CH₃ | H | CH₃ | H | H | H | H | H | H | 194 | II |
| 17 | CO₂CH₃ | H | CN | H | H | H | H | H | H | H | H | 82 | II |
| 18 | CO₂CH₃ | H | CH₂Ph | H | H | H | H | H | H | H | H | 140 | II |
| 19 | CO₂CH₃ | H | COPh | H | H | F | H | H | H | F | H |  | II |
| 20 | CO₂CH₃ | H | CONH₂ | H | H | H | H | H | H | H | H | 117 | II |
| 21 | CO₂CH₃ | H | H | H | H | H | H | CO₂CH₃ | H | H | H | 179 | II |
| 22 | CO₂CH₃ | H | CO₂CH₃ | H | H | H | H | H | H | H | H | 106 | II |
| 23 | CO₂CH₃ | H | CO₂CH₃ | H | H | H | CO₂CH₃ | H | H | H | H | 159 | II |
| 24 | CO₂CH₃ | —(CH₂)₃— | | CH₃ | CH₃ | H | H | H | H | H | H | 200 | II |
| 25 | CO₂CH₃ | —(CH₂)₄— | | CH₃ | CH₃ | H | H | H | H | H | H | 158 | II |
| 26 | CO₂CH₃ | —(CH₂)₄— | | —(CH₂)₄— | | H | H | H | H | H | H | 166 | II |
| 27 | CN | H | CO₂C₅H₁₁ | H | H | H | H | H | H | H | H | 127 | III |
| 28 | CO₂CH₃ | H | H | H | H | H | H | CO₂C₂H₅ | H | H | H | 176 | II |
| 29 | CO₂C₇H₁₅ | CH₃ | C₄H₉ | H | CH₃ | H | H | H | H | H | H | 52 | II |
| 30 | CO₂C₆H₁₁ | H | H | H | H | H | H | H | H | H | H | 72 | II |
| 31 | CP₂C₆H₁₁ | CH₃ | H | H | CH₃ | H | H | H | H | H | H | 58 | II |
| 32 | CO₂C₆H₁₁ | H | Benzo | | H | H | H | H | H | H | H | 58 | II |
| 33 | CO₂CH₃ | H | H | H | H | Benzo | H | | Benzo | | H | | |
| 34 | CO₂CH₃ | H | H | H | H | Benzo | H | H | Benzo | | | | |

B. Use of the compounds

EXAMPLE 1

A concentrated solution of [pentyl 6',7'-dicyanospiro|9H-fluorene-9,5'(4'aH)-pyrrolo[1,2-b]pyridazine]-3'-carboxylate] (prepared according to DE-A1-3,521,432) in toluene is added to a glass plate provided with vapor-deposited interdigital electrodes (distance between the electrodes 1 mm). An electrical field of 1.5 kV/mm is applied to the electrodes and the plate is simultaneously irradiated with UV light. After evaporating the solvents in the applied electrical field, a thin layer of the red betaine compound remains which possesses non-linear optical properties of the second order. This layer causes, on oblique transverse irradiation with light from a NdYAG laser, partial doubling of the frequency of the irradiating light.

EXAMPLE 2

A solution of polymethyl methacrylate PMMA (40% by weight) and pentyl [6',7'-dicyanospiro[9H-fluorene-9 5'(4'aH)pyrrolo[1,2-b]pyridazine]-3'-carboxylate] (2% by weight) in toluene is applied by spin-coating to a glass plate provided with interdigital electrodes according to example 1. The toluene is allowed to evaporate at room temperature. The polymer film obtained is heated to 105° C. and an electrical field of 1.5 kV/mm is applied, the polymer film being irradiated with UV light at the same time. After 5 min, the polymer film is cooled to room temperature in the electrical field. A transparent, red polymer film having non-linear optical properties of the 2nd order remains.

EXAMPLE 3

A solution of pentyl 6',7'-dicyanospiro[9H-fluorene-9,5'(4'aH)-pyrrolo[1,2-b]pyridazine]-3'-carboxylate (1%) and poly-4-(4'-cyanobiphenyl(4)-oxycarbonyl)-phenoxyethyl methacrylate (20%) in N-methylpyrrolidone is applied to a glass plate provided with interdigital electrodes by spin-coating. The N-methylpyrrolidone is allowed to evaporate at elevated temperature. The polymer film is heated to 150° C. and otherwise treated as in the preceding example to give a transparent, red, orientated liquid crystal polymer film having non-linear optical properties of the 2nd order.

EXAMPLE 4

A mixture of 2.17 g of pentyl 6',7'-dicyanospiro[9H-fluorene-9,5'(4'aH)-pyrrolo[1,2-b]pyridazine]-3'-carboxylate, 2.0 g of 1,10-decanediol and 0.75 ml of titanium tetraisopropanolate is heated to 80° C. and the resulting solution is held at this temperature for 7 h. The reaction mixture is cooled to about 40° C., 1N HCl is added and the mixture is extracted with dichloromethane. The organic phase is dried over Na₂SO₄ and evaporated. The residue is chromatographed on a silica gel column to give yellow crystals of 10-hydroxydecyl 6′,7′-dicyanospiro[9H-fluorene-9,5′(4′aH)-pyrrolo[1,2-b]pyridazine]-3′-carboxylate.

EXAMPLE 5

A solution of 929 mg of dicyclohexylcarbodiimide in 1 ml of dichloromethane is added dropwise to a solution of 2.08 g of 10-hydroxydecyl 6′,7′-dicyanospiro[9H-fluorene9,5′(4′aH)pyrrolo[1,2-b]pyridazine]-3′carboxylate, 344 mg of methacrylic acid, 49 mg of 4-dimethylaminopyridine and 1 mg of 2,6-di.tert-butyl-4-methylphenol in 10 ml of dichloromethane kept at 0° C. and the mixture is stirred at RT for 2 h. The precipitate is filtered off with suction, the filtrate is concentrated and the residue is chromatographed to give 10-methacryloyloxydecyl 6′,7′-dicyanospiro[9H-fluorene-9,5′(4′aH)-pyrrolo[1,2-b]pyridazine]-3′-carboxylate as yellow crystals.

EXAMPLE 6

A solution of 294 mg of 10-methacryloyloxydecyl 6′,7′dicyanospiro[9H-fluorene-9,5′(4′aH)-pyrrolo[1,2-b]pyridazine]-3′-carboxylate, 951 mg of methyl methacrylate and 50 mg of azobisisobutyronitrile in 20 ml of toluene is
heated to 60° C. for 20 h under $N_2$ and the polymer is precipitated twice from ethanol to thus give a yellowish polymer. A film having non-linear optical properties is prepared from this polymer analogously to Example 2.

EXAMPLE 7

A solution of 294 mg of 10-methacryloyloxydecyl 6′,7′-dicanospiro[9H-fluorene-9,5′(4′aH)-pyrrolo[1,2-b]pyridazine]-3′-carboxylate, 4.06 g of 4-(4′-cyanobiphenyl(4)-oxycarbonyl)-phenoxyethyl methacrylate and 50 mg of azobisisobutyronitrile in 30 ml of N-methylpyrrolidone is heated to 60° C. for 20 h under $N_2$ and the polymer is precipitated twice from ethanol to give a yellowish polymer. Treatment of this polymer analogously to Example 3 gives an orientated liquid crystal polymer film having non-linear optical properties.

EXAMPLE 8

A solution of 1 g of 3-(4-pyridazyl) acrylmethacrylate (sic) and 0.9 g of dibenzoyl peroxide in 19 g of methyl methacrylate (molar ratio of the ester 1:31) is allowed to stand at 60° C. for 29 hours. The mixture is subsequently dissolved in dichloromethane and precipitated from methanol to give poly(methyl 3-pyridazin-4′-yl) acrylate co-methyl methacrylate as a faintly yellow polymer.

EXAMPLE 9

0.5 g of 1,2-dimethoxycarbonylspiro[cyclopropene-3,9′-fluorene] is added to a solution of 4.6 g of the copolymer from Example 8 in 20 ml of dichloromethane. Stirring the solution for 48 hours with the exclusion of light gives poly(methyl 3-6′,7′-dicarboxymethylspiro[9H-fluorene-9,5′(4′aH)-pyrrolo[1.2-b]-pyridazin]3′-yl)acrylate comethyl methacrylate as a yellow polymer.

We claim:

1. In a device for displaying a non-linear optical effect, said device containing a non-linear optical material, the improvement wherein said non-linear optical material comprises, at least one component containing the structure of a pyrrolo[1.2-b]azine radical of the formula I and/or its valence isomers of the formula I′

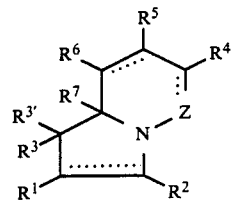

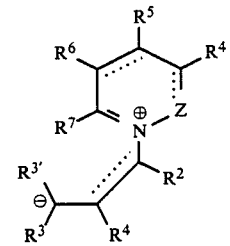

in which one of the double bonds represented as dashes can be a single bond between the positions 2–3, 5–6, and 7–8, and wherein $R^1$ is $C_1$-$C_{10}$-alkoxycarbonyl, $C_1$-$C_{10}$-alkanoyl, $C_7$-$C_{11}$-aroyl, —CN, —CF$_3$, —N($C_{1-4}$-alkyl)$_2$ or H, if $R^2$ is not also H at the same time;

$R^2$ is H or a radical $R^1$;

$R^3$ and $R^{3'}$ are a radical completing a dibenzocyclopentadiene ring, dichlorobenzocyclopentadiene ring, monobenzodiphenylcyclopentadiene ring, tetraphenylcyclopentadiene ring, dibenzocyclohexa-2,5-diene-4-one ring or its 4-thione, indan-1,3-dione-2,2-diyl ring, 2,2-dimethyl-1,3-dioxane-4,6-dione-5,5-diyl ring, or of a dibenzo-γ-pyran ring, or $R^3$ and $R^{3'}$ are each, independently from one another, phenyl, $C_{1-10}$-alkoxycarbonyl, $C_{1-10}$-alkanoyl, 4-nitrophenyl, 4-cyanophenyl or $C_1$-$C_{10}$-alkoxy-propenoyl, or one of the radicals is also H;

$R^4$ is H, $C_1$-$C_{10}$-alkyl or, together with $R^5$, a radical completing a fused cyclopentane or cyclohexane ring;

$R^5$ is H, $C_1$-$C_{10}$-alkyl, $C_{1-10}$-alkoxy, $C_{1-10}$-alkoxycarbonyl, —CN, —CH$_2$Ph, —COPh, —CONH$_2$, —CON—($C_{1-4}$-alkyl)$_2$, —CONH($C_{1-4}$-alkyl) or, together with $R^4$, is a radical completing a fused cyclopentane or cyclohexane ring or, together with $R^6$, a radical completing a fused benzene ring;

$R^6$ is H, $C_{1-10}$-alkyl or, together with $R^5$, a radical completing a fused benzene ring or, together with $R^7$, a radical completing a fused cyclopentane or cyclohexane ring;

$R^7$ is H, $C_{1-10}$-alkyl or, together with $R^6$, a radical completing a fused cyclopentane or cyclohexane ring; and Z is —N=, —CR$^4$= or —CHR$^4$—, with the proviso that if Z is —CR$^4$= or —CHR$^4$—, then $R^4$ is H or $C_{1-10}$-alkyl, wherein said material exhibits non-linear optical effects.

2. A device according to claim 1, comprising a layer of at least one compound of the formula I applied to a substrate.

3. A device according to claim 1, comprising at least one polymeric component, wherein at least one further component is a compound of the formula I.

4. A device according to claim 1, wherein said radical contains double bonds between the positions 2-3, 5-6, and 7-8.

5. A device according to claim 1, wherein $R^1$ and $R^2$ are each $C_1$-$C_{10}$-alkoxycarbonyl, —CN, or —N($C_1$-$C_4$-alkyl)$_2$.

6. A device according to claim 1, wherein $R^3$ and $R^{3'}$, identically or different, are $C_1$-$C_{10}$-alkoxycarbonyl, phenyl, 4-nitrophenyl, or 4-cyanophenyl.

7. A device according to claim 1, wherein $R^3$ and $R^{3'}$ together are a dibenzocylopentadiene ring.

8. A device according to claim 1, wherein $R^5$ is H, $C_1$-$C_{10}$-alkyl, $C_1$-$C_{10}$-alkoxycarbonyl, —CN, —CH$_2$Ph, —COPh, —CONH$_2$ or, together with $R^4$, is a radical completing a cyclopentane or cyclohexane ring or, together with $R^6$, is a radical completing a benzene ring.

9. A device according to claim 1, wherein $R^6$ is H, $C_1$-$C_5$-alkyl or, together with $R^5$, is a radical completing a benzene ring or, together with $R^7$, is a radical completing a cyclohexane ring.

10. A device according to claim 1, wherein $R^7$ is H, $C_1$-$C_5$-alkyl or, together with $R^6$, is a radical completing a cyclohexane ring.

11. A device according to claim 1, wherein Z is —N= or —CR$^4$=.

12. A device according to claim 1, wherein said radical is pentyl-6',7'-dicyanospiro[9H-fluorene-9,5'(4'aH)-pyrrolo[1,2-b]pyridazine]-3'-carboxylate.

13. A device according to claim 1, comprising at least one polymeric component, wherein said polymeric component is doped with a pyrrolo[1.2-b]azine radical of Formula I.

* * * * *